United States Patent [19]

Polz

[11] Patent Number: 5,924,989
[45] Date of Patent: Jul. 20, 1999

[54] METHOD AND DEVICE FOR CAPTURING DIAGNOSTICALLY ACCEPTABLE THREE-DIMENSIONAL ULTRASOUND IMAGE DATA RECORDS

[76] Inventor: Hans Polz, Emil Amer Strasse 2, D-85456 Wartenberg, Germany

[21] Appl. No.: 08/828,582

[22] Filed: Mar. 31, 1997

Related U.S. Application Data

[63] Continuation-in-part of application No. 08/626,753, Apr. 2, 1996., abandoned

[30] Foreign Application Priority Data

Apr. 3, 1995 [DE] Germany .............................. 195 12 397
Mar. 8, 1996 [DE] Germany .............................. 196 08 971

[51] Int. Cl.$^6$ ....................................................... A61B 8/00
[52] U.S. Cl. ............................................ 600/443; 128/916
[58] Field of Search ...................................... 600/443, 449; 128/916

[56] References Cited

U.S. PATENT DOCUMENTS

| | | | |
|---|---|---|---|
| 4,100,916 | 7/1978 | King ......................................... | 128/916 |
| 5,197,476 | 3/1993 | Nowacki et al. . | |
| 5,241,473 | 8/1993 | Ishihara et al. . | |
| 5,295,483 | 3/1994 | Nowacki et al. . | |
| 5,315,512 | 5/1994 | Roth .................................... | 128/660.07 |
| 5,353,354 | 10/1994 | Keller et al. ........................ | 364/413.25 |
| 5,398,691 | 3/1995 | Martin et al. ........................... | 128/916 |
| 5,538,004 | 7/1996 | Bamber .................................... | 128/916 |

FOREIGN PATENT DOCUMENTS

| | | |
|---|---|---|
| 0620448 | 10/1994 | European Pat. Off. . |
| 3908648 | 9/1990 | Germany . |
| 4224568 | 1/1993 | Germany . |
| 4306037 | 9/1994 | Germany . |

OTHER PUBLICATIONS

De–Z: Deutsche medizinische Wochenschrift, 117, 1992, Seiten 467 bis 472.

DE: Zeitschriften–Ubersicht, Amer. J. Obstet. Gynecol. Fortsetzung S.37 (nach Seite 474) —Accupro 5/10/20 Feb. 1991.

3 Space—Isotrak II—Polhemus—3 pages Jul. 1995.

*Primary Examiner*—Francis J. Jaworski
*Attorney, Agent, or Firm*—Bierman, Muserlian and Lucas

[57] ABSTRACT

A method and apparatus for generating a diagnostically usable three-dimensional image data set is disclosed. The ultrasonic images generated from an ultrasonic apparatus are supplied to an image processing system which uses a position sensor system to determine the spatial location of the ultrasonic image in each dimension. The raw data are transformed into three-dimensional data set having numerous voxels with associated image or gray values, the image or gray values being formed for each voxel according to a preassigned algorithm, to wit from the image or gray values of those image points which are closest in each instance to the current voxel in the unit images or their image planes and whose distance from the current voxel does not exceed a preassigned maximum allowable distance.

24 Claims, 7 Drawing Sheets

METHOD AND DEVICE FOR CAPTURING DIAGNOSTICALLY ACCEPTABLE THREE-DIMENSIONAL ULTRASOUND IMAGE DATA RECORDS

CROSS-REFERENCES TO RELATED APPLICATIONS

The instant application is a continuation-in-part of application Ser. No. 08/626,753 filed Apr. 2, 1996 and now abandoned.

BACKGROUND OF THE INVENTION

1. Field of the Invention

The present invention relates to a method for generating a diagnostically acceptable three-dimensional image data record with the use of an ultrasound unit with a freely guided ultrasound head for generating a sequence of a plurality of ultrasound images of the volume to be examined, with the use of an image-processing system connected to the ultrasound unit, to which the sequence of the ultrasound images generated is supplied, and with the use of a position-sensor system which determines the position and orientation of the ultrasound head and hence the spatial location of the image plane of the ultrasound image generated in each instance, specifically with regard to the three degrees of freedom of translation and rotation, where these position and orientation data of the sensor system are likewise transmitted to the image-processing system, which generates the three-dimensional data record tomographically capturing the examined volume from image data of ultrasound images and position and orientation data, and a device for generating such a diagnostically acceptable three-dimensional image data record.

2. Description of the Related Art

Such a method and device are well known in principle (U.S. Pat. No. 4,100,916). In this known method, individual ultrasound images are defined with respect to their location in space in consideration of position and orientation data that are determined by a sensor system working by ultrasound. A three-dimensional diagnostically acceptable data record that permits capture of a tomographic image of a volume to be examined is not generated.

SUMMARY OF THE INVENTION

The object of the invention is to demonstrate a device by which it is possible, with free manual guidance of the ultrasound converter, to effect tomographic capture, by a three-dimensional data record, of an entire volume or three-dimensional space to be examined.

To accomplish this object, a method is executed according to the characterizing portion of claim 1, and a device is designed according to the characterizing portion of claim 9.

In the invention, upon free guidance of the ultrasound converter along a volume to be examined for tomographic image capture, a three-dimensional data record is generated which, in accordance with the tomographic image capture, consists of a plurality of individual images that cover the entire volume to be examined and in turn are composed of a plurality of image values.

BRIEF DESCRIPTION OF THE DRAWINGS

The invention is explained in detail below by an example, with the aid of the figures, wherein.

DESCRIPTION OF THE PREFERRED EMBODIMENTS

Figure 1:
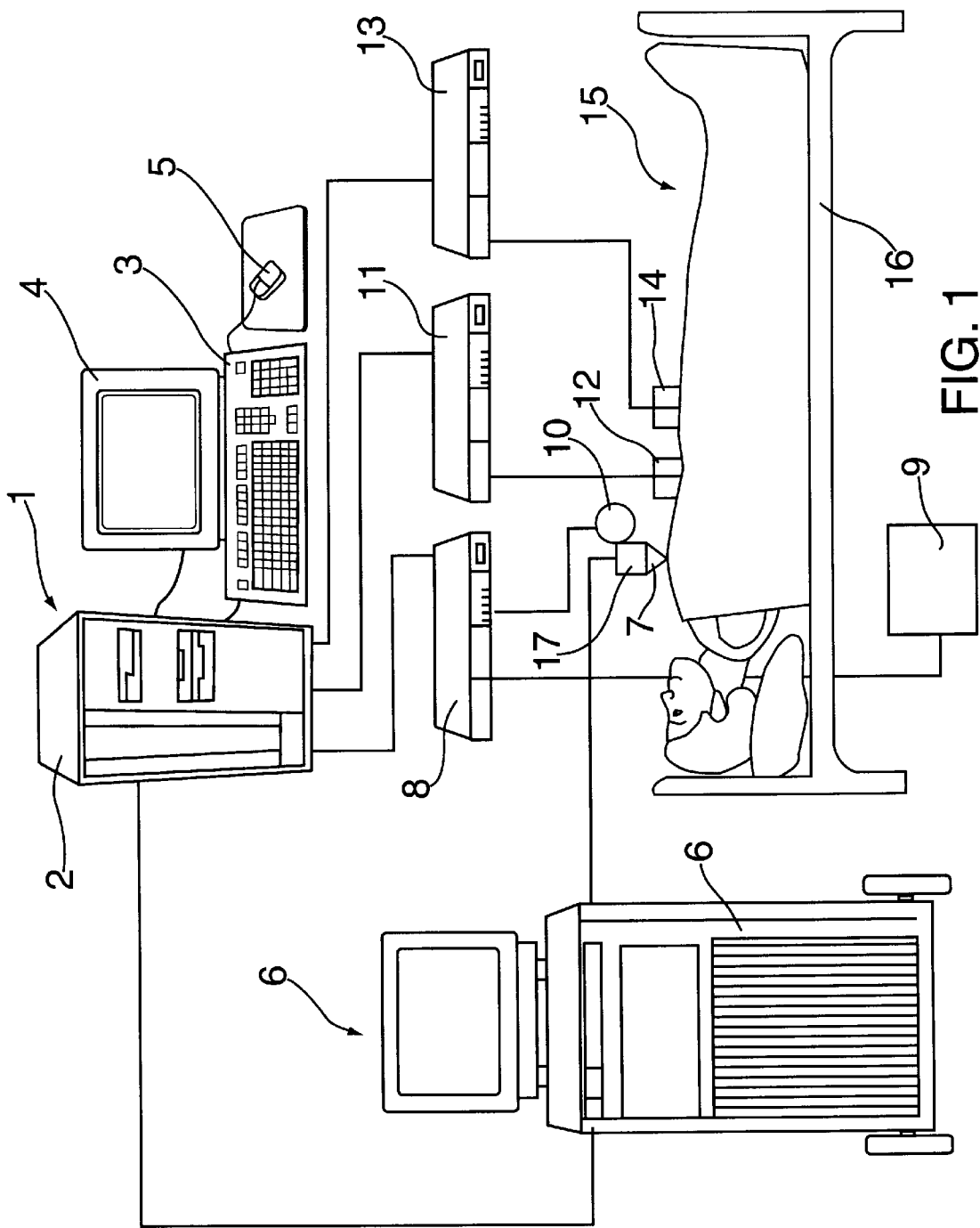
FIG. 1 shows, in schematic representation, an embodiment of the device according to the invention for generating diagnostically acceptable three-dimensional data records for capture of a tomographic image of a volume to be examined.

In FIG. 1, 1 is an image-processing system consisting essentially of the computer 2 and of the peripheral devices connected to it, such as keyboard 3, display screen 4 and mouse control 5, etc.

Added to this image-processing system are:

An ultrasound unit 6 with ultrasound head 7;

an electromagnetic location or position-detecting device or an electromagnetic sensor 8 with a transmitter 9 and a receiver 10 formed of magnetic coils;

an electrocardiograph 11 with associated electrodes 12;

a device 13 for recording the respiratory position (respiratory cycle) with associated probes 14.

A patient, whose body or body region forms a volume to be examined, is labeled 15. The patient 15 is arranged on a couch 16.

The ultrasound unit 6 with the ultrasound head 7 is a device well known to persons skilled in the art and is used in medical diagnosis for producing ultrasound images which each reproduce a region of the volume to be examined, which is located in the image plane of the freely guided ultrasound head 7. On the ultrasound head 7, which is freely guided manually by the examiner (physician), there is preferably provided a holder 17, on which the receiver 10 of the sensor system 8 is alternatively located.

Because of the magnetic fields radiated by the transmitter 9, which are detected by the receiver 10 or the coils there, the system supplies sensor data (raw position and rotation data) at its output, by which the position and orientation in space of the receiver 10 are precisely defined, specifically, by translation data in the X, Y and Z axes as well as by rotation data about these axes.

Such an electromagnetic sensor system is familiar to persons skilled in the art, specifically, as for example ISOTRAK II, of the Polhemus firm, One Hercules Drive, P.O. Box 560, Colchester, Vt. 05446.

Figure 2:
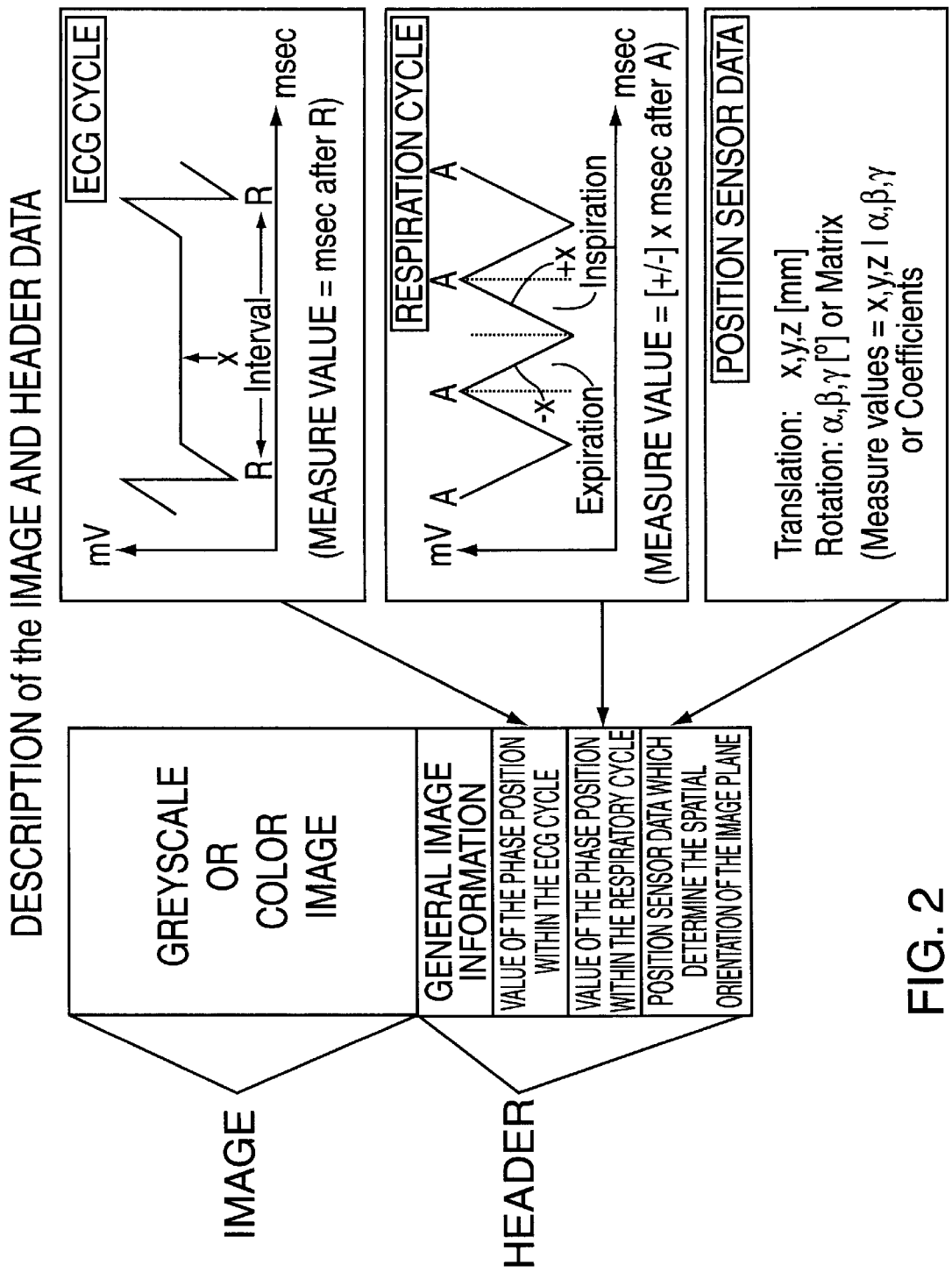
FIG. 2, in schematic representation, individual images stored shows in the image-processing system, together with graphic representations of a patient's ECG cycle and respiratory cycle.

The electrocardiograph 11 is a device which is familiar to persons skilled in medical practice and diagnosis and which at an output delivers a varying voltage as a function of the ECG cycle, which is reproduced in diagram a of FIG. 2 and has typical positive and negative R waves, between each of which an R interval is formed. The device 13 likewise is a device familiar to persons skilled in the art, which is used in medical practice and diagnosis for recording the respiratory cycle and as a function of this respiratory cycle supplies a varying voltage at its output, which is reproduced in diagram b of FIG. 2.

As is also shown in FIG. 2, for each individual image, in addition to the image contents, an associated image header which contains additional information, for example general information concerning the image, a measured value that determines the respective phase position of the image in the ECG cycle, a measured value that determines the phase position of the respective image in the respiratory cycle, and position and orientation data that determine the location of the image plane of the respective individual image in space, is alternatively stored in the image-processing system 1, in digital form.

In order to obtain a defined location or position relationship of the respective image plane, the electromagnetic sensor system 8 is used, whose receiver 10, which has at least one receiving coil, is provided on the holder 17 of the freely guided sound converter or ultrasound head 7, specifically, in a predetermined spatial relationship to the active part or image plane of this sound converter.

For generating position and orientation data (translation data for X, Y and Z axes as well as rotation data about these axes), the spatial relationship between the image plane of the ultrasound head 7 and the receiver of the sensor system is then calculated by calibration, i.e., with the use of special calibration parameters. This then makes it alternatively possible, inter alia, to use the holder 17 with the receiver 10 on a variety of ultrasound heads and to take these into account in each instance by individualized calibration or conversion of the raw position data supplied by the receiver of the sensor system.

Thus calibration takes into account the geometric position relationship between the receiver and the orientation of the active part (crystal) of the ultrasound head 7 or of the plane (image plane) in which the image produced by the ultrasound head 7 lies.

For capture of images the actual position of the respective image plane in space does not matter; for tomographic image capture it is sufficient to capture the position of individual image planes relative to one another. Accordingly, the transmitter 9 of the sensor system 8 may be positioned as desired in the field surrounding the device.

Hence the sensor system 8 computes the position and orientation values—defined by the three degrees of freedom of translation (X, Y and Z axes) and by the three degrees of freedom of rotation—and establishes these data in the image-processing system, which by calibration computes the true position and orientation data from these raw position and orientation data, the true data then being assigned to the respective image contents.

The individual images are supplied by the ultrasound system 6, in a predetermined chronological order (sequence), as an analog or digital image or video sequence to the input of the image-processing system 1 located downstream. When this system is turned on or activated, the images, which for example are half-images or full images, are digitized in the image-processing system 1 (in analog video sequence) or else taken over in digital form (in digital video sequence) and, with the associated image header or header data, stored digitally in a memory of the image-processing system 1 (image input).

Image input into the image-processing system 1 is triggered by the user of the device (for example, by actuating a foot switch). Likewise, image input is ended, for example by the user or else automatically by the image-processing system 1, when the three-dimensional data record formed by the plurality of individual images with the associated header in each instance has reached a predetermined size.

If, for example, this predetermined size is 30 megabytes, this means that with a size of each individual image of 256×256 pixels and with a greyscale of 8 bits as well as with an input of 50 half-images per second, after about 8 seconds and after an input of 457 individual images the memory volume is filled and image input is then automatically ended by the image-processing device. The use of image masking permits input of greater image quantities by reducing the memory requirements per individual image.

Figure 6:
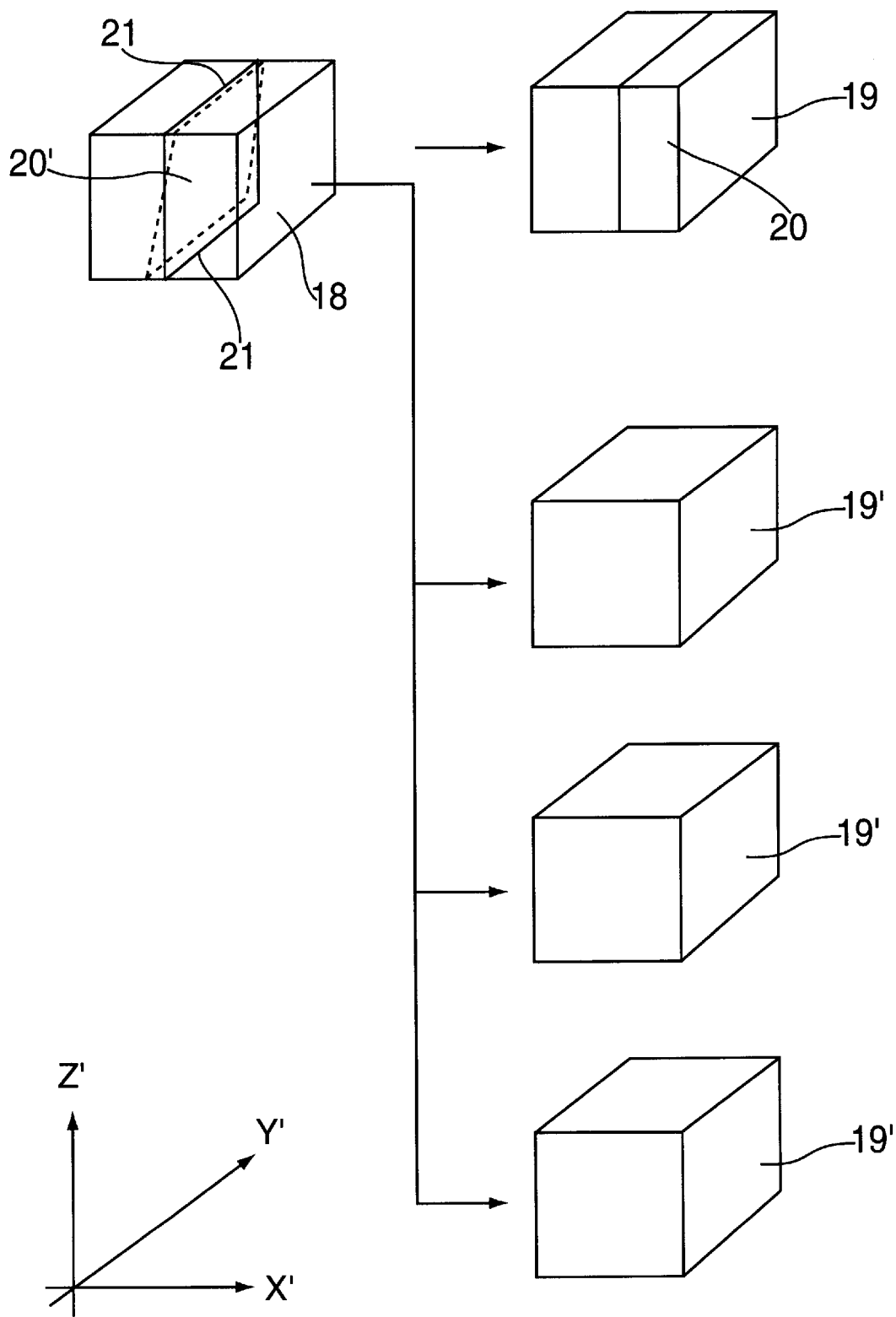
FIG. 6, shows a schematic representation of the transformation of raw data into an acceptable three-dimensional data record.

Since the image planes of individual images are very variably oriented in space by the free guidance of the ultrasound head, during image storage, i.e., in a data capture or acquisition phase, storage of individual raw image data is first effected as raw data record 18 (FIG. 6). After image input is ended, transformation of these raw data then takes place in the image-processing system 1, with the use of a special program, into a common reference system, for example, a system of Cartesian coordinates with the axes X', Y' and Z' (FIG. 6), in order thus to obtain for later use an acceptable three-dimensional data record 19 relating to the volume examined.

In principle, this three-dimensional digital data record 19 is produced so that it contains a plurality of individual volume elements 20 (voxels) which, in this data record 19, have a predetermined location with regard to the common reference system (X', Y' and Z' axes). In this transformation, each image point 20' of the images forming the raw data 18 is filed away in its proper position in a corresponding voxel 20 of this three-dimensional data record. If a particular region of the volume to be examined has not been captured upon image capture, no image value can be assigned to the corresponding voxel 20 upon transformation either, i.e., the three-dimensional data record 19 would then contain gaps which, however, can be filled in by interpolation.

But the possibility also exists that particular regions of the volume to be examined have by accident been multiply scanned upon image capture and that particular image values 20' are then redundant. In this case, either the formation of an average value for redundant image values takes place in the image-processing system 1 or else, according to a selection routine, only one image value continues to be used.

The device according to the invention is alternatively suitable in especially advantageous fashion for tomographic image capture of organs in motion, in particular of organs whose motion is directly related to the beating of the heart (e.g., cardiac vessels), specifically, again with free guidance of the ultrasound converter.

In principle, here the possibility exists of generating a static three-dimensional data record of such tissue and thereby preventing geometric distortions resulting from the motion, for example, cardiac activity. In this case, input of images by the image-processing system 1 takes place synchronously with the cardiac cycle or with the positive or negative R wave of the cardiac cycle of the person to be examined. The cardiac cycle and the R wave are determined by means of an electrocardiograph 11, to which probes 12 on the patient 15 are connected. Triggering causes every image input to be effected in a precisely defined time window within the cardiac cycle, i.e., in each instance every image input takes place in a defined interval of time (phase position) after appearance of the respective R wave in the ECG cycle used for triggering. This means that all individual images stored in the image-processing system 1 and forming the raw data are then synchronous in phase with the cardiac cycle, so that these individual images can be converted into a three-dimensional static data record 19 which or whose individual voxels 20 have no geometric distortions.

By varying the phase position of the time window for image input in regard to the triggering R wave, three-dimensional tomographic data records 19 of the volume examined can be generated, which records in each instance reproduce the said volume at variable times in the ECG cycle.

In addition, dynamic three-dimensional data records 19 of the volume examined, namely, of organs in motion, etc., may likewise be made with the device according to the invention. In this case, input of images by the image-processing system does not take place synchronously with the cardiac cycle, but independently of it. Here too, the measured value that determines the phase position in the ECG cycle is again stored in the image header of each individual image 21.

This three-dimensional dynamic data record 19, which again is obtained by transformation of the raw data 18 into a common reference system, consists, for example, of a plurality of partial data records 19', each of which captures the total volume to be examined and is itself composed of a plurality of volume elements 20, the partial data records 19' reproducing the volume examined but in each instance at variable times in the ECG cycle.

Generation of the dynamic three-dimensional data record 19 is effected, for example, for a complete ECG cycle or else alternatively for only part of such a cycle, images or image values in varying ECG cycles being used for generation of this data record 19, specifically, so that after or upon transformation of the raw data 18 all image values present in varying ECG cycles are in each instance arranged in correct position in the voxels 20 of the partial data record 19' corresponding to their phase position.

If image values are missing upon generation of the partial data record 19' because regions of the volume examined have not been captured in image capture, such gaps may again be filled in by the image-processing system by interpolation. If a plurality of image values is present in a given voxel 20, this coincidence is again removed by the formation of an average value or by the elimination of certain image values cr by a combination of the two methods.

Three-dimensional data records 19 may alternatively be generated as static or dynamic data records of organs or body parts which are subject to passive motion, for example, by breathing. For this, the device 13, which captures the patient's respiratory position or respiratory cycle, is connected to the image-processing system 1. This respiratory cycle, which is reproduced in FIG. 2 in diagram b, in each instance consists of the expiratory phase (exhalation phase) and the inspiratory phase (inhalation phase). For the generation of a static three-dimensional data record 19 undistorted by passive motion, the image-processing system 1 can again be triggered by or synchronized with this respiratory cycle, for example, with the A waves there, specifically, so that image input in each instance takes place only during a predetermined window in the respiratory cycle. In principle, control may also be effected in such fashion that image input takes place only with the respiratory position is not activated, i.e., no respiratory signal is present.

In principle, a dynamic three-dimensional data record may alternatively be generated taking the respiratory position into account, the respiratory cycle then being used in the way described above for the ECG cycle for generation of the dynamic data record 19.

Figure 3:
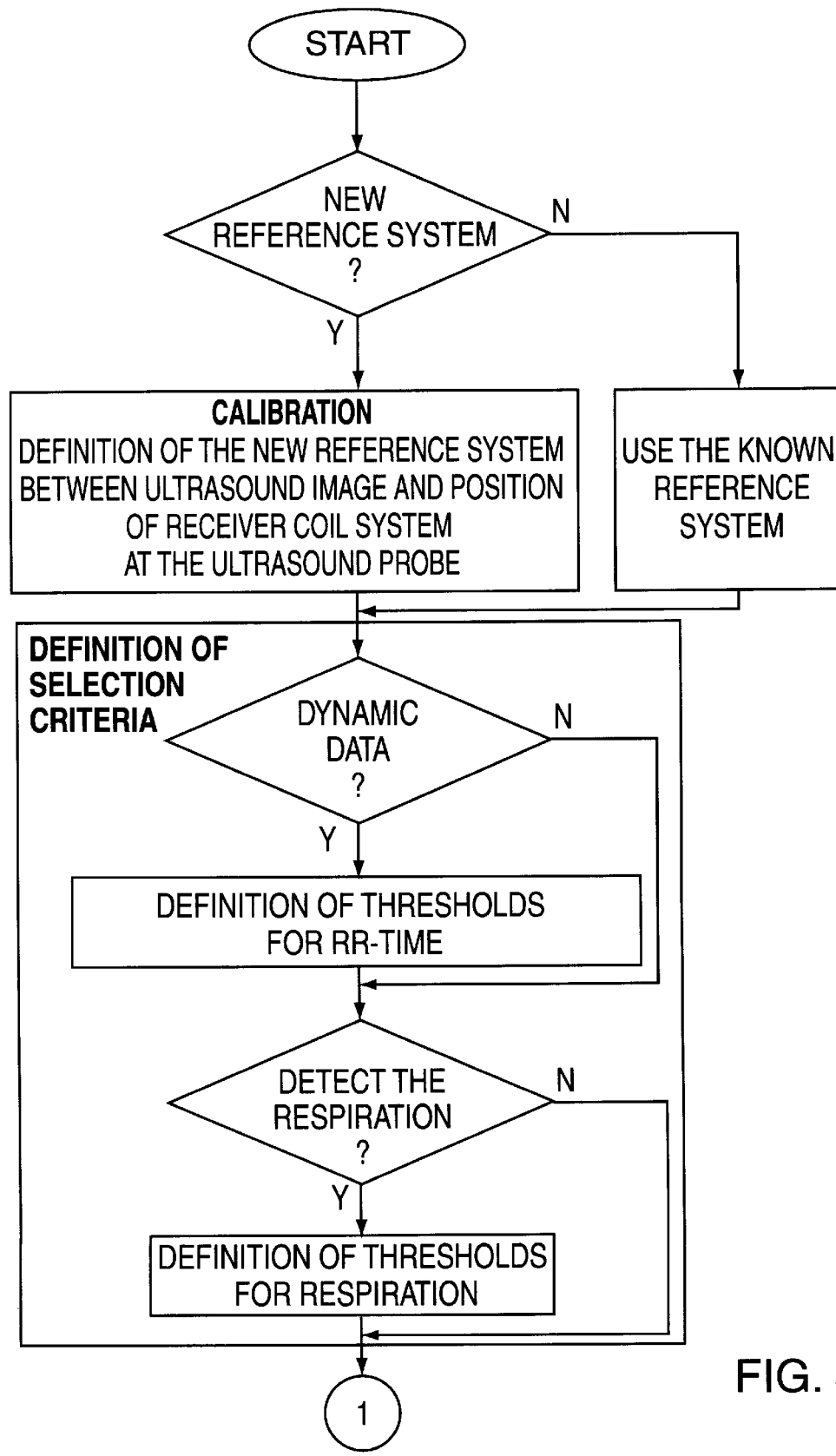
FIGS. 3–5, show a flow chart of operation of the device according to the invention.
Figure 4:
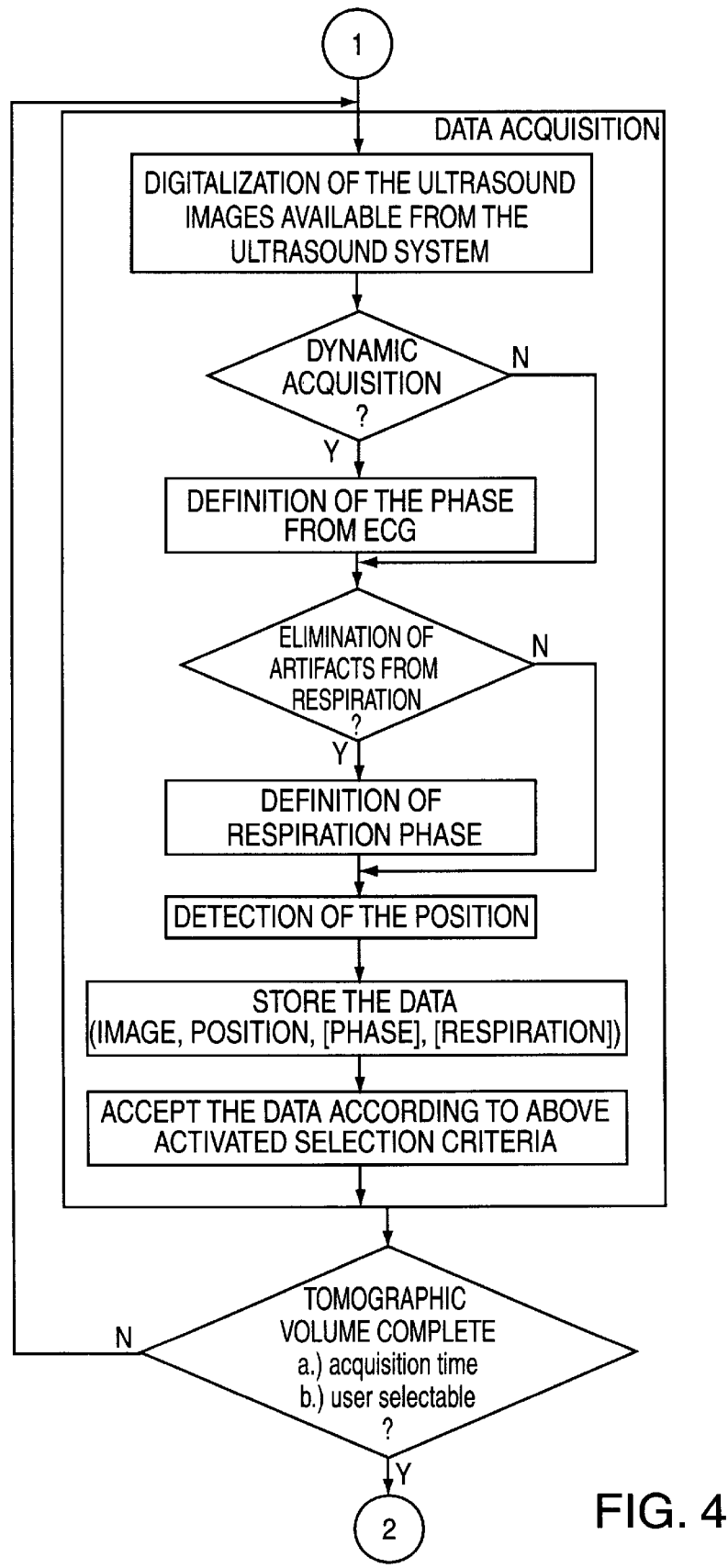
Figure 5:
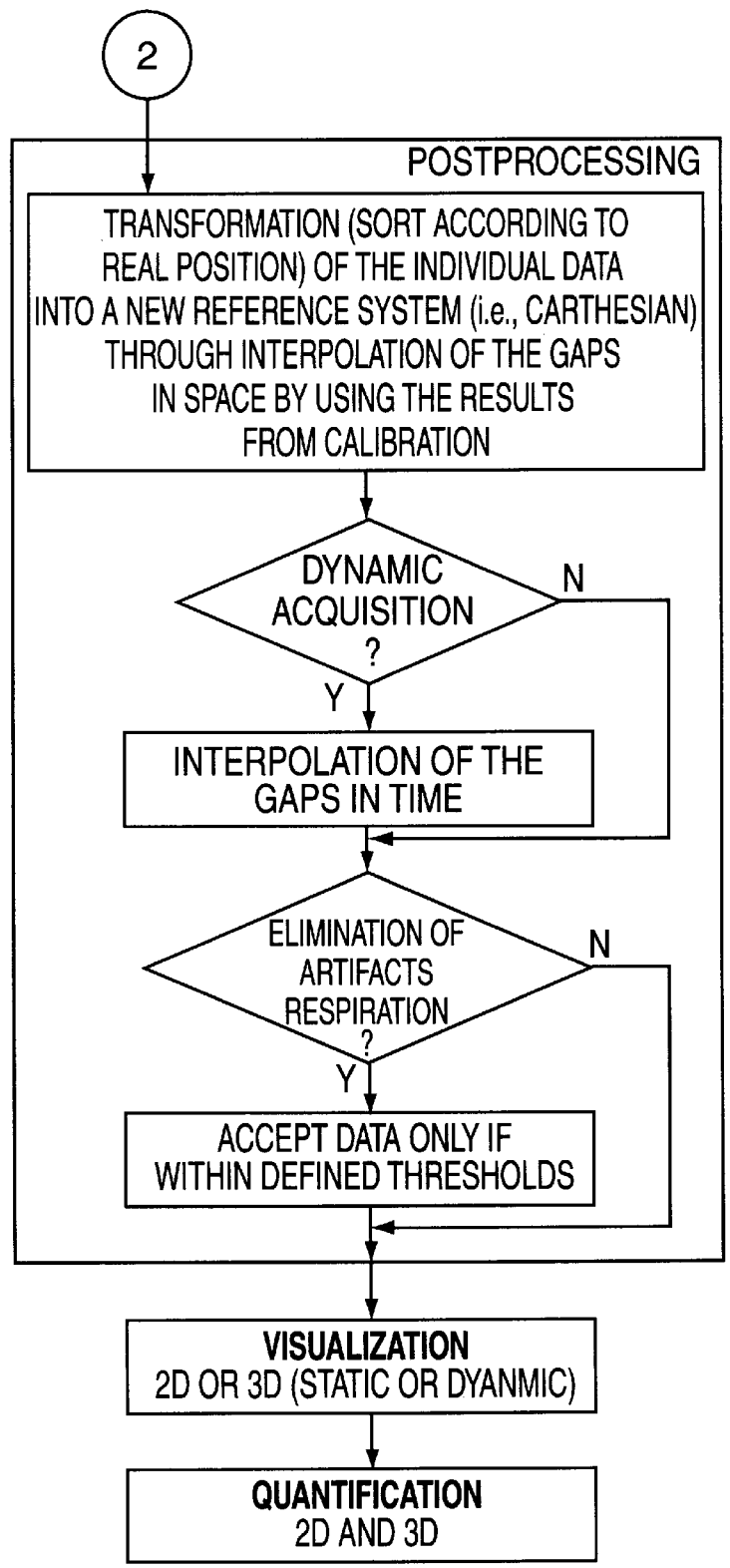

In a flow chart FIGS. 3–5 show the operation of the device according to the invention in greater detail.

FIG. 3 concerns the initial setup particularly of the image-processing system 1 before the capture of images (data acquisition). First it is decided whether the reference system, i.e., the spatial coordination between the image plane of the ultrasound head 7 and the receiver 10, must be recalibrated, especially because of the use of a new ultrasound head 7 which has not yet been employed in the system.

If a new reference system is necessary, appropriate calibration is undertaken. If a known reference system can be employed, it or its calibration may be used. The next step is definition of possible selection criteria. If dynamic data capture in consideration of cardiac activity is to take place, a threshold value with regard to the magnitude of the R—R interval is set. This setting is unnecessary when dynamic data capture is not desired. Then comes the decision about whether the respiratory position is to be taken into account. If so, the threshold value with regard to the respiratory position is defined, for example, by setting a maximum and minimum threshold value for the duration of a respiratory cycle. Definition of the threshold value is omitted when the respiratory position is not to be taken into account.

After such preliminary setting, data capture or acquisition according to FIG. 4 takes place. First the ultrasound images supplied by the ultrasound head 7 are digitized. Then for dynamic data capture the phase position in the ECG cycle and/or the phase position in the respiratory cycle is determined, this determination being omitted when dynamic data acquisition or data acquisition with consideration of the respiratory position is not desired.

In every case, position recognition is effected at each image input. The image data captured are then stored together with the additional data as raw data record 18, while the additional data (measured value for the phase position in the ECG cycle, measured value for the phase position in the respiratory cycle and position data) are stored in the image header.

Then examination of the data is effected by means of the selection criteria found in the method step of FIG. 3. Any data which do not meet these selection criteria are rejected and removed.

Data acquisition is ended when the tomographic volume to be examined is complete, which is established either automatically by the image-processing system according to a time criterion or else by the user.

If the tomographic volume is not complete, the method steps of FIG. 4 are executed anew.

Figure 7:
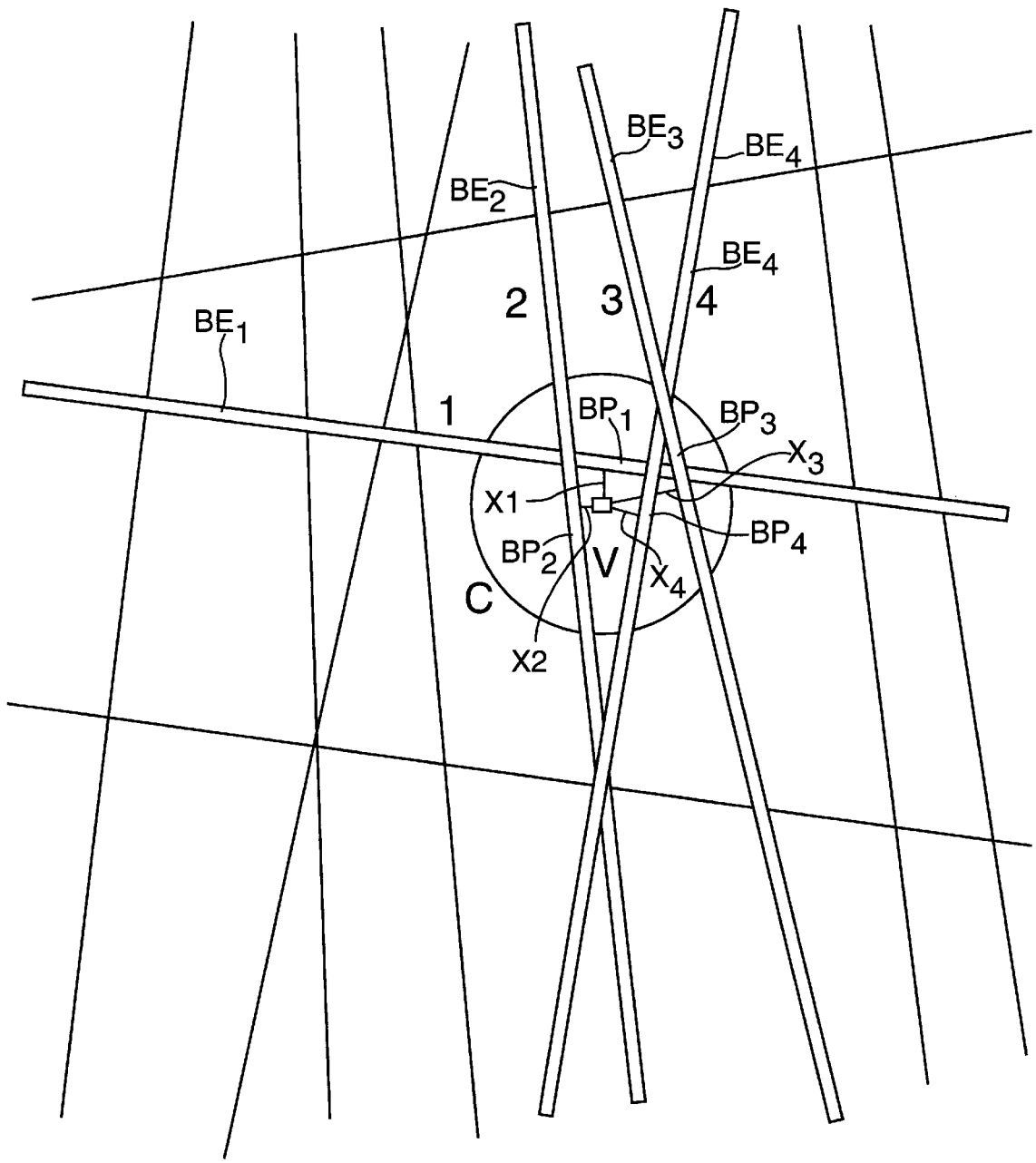
FIG. 7 shows a schematic representation for explaining the transformation of the raw data into the three-dimensional data record.

FIGS. 5 to 7 illustrate the transformation of the raw data 18 into the data set 19. As has already been explained above, using the sensor 17, first individual images, i.e. two-dimensional individual images 21 in different image planes (depending on the positioning of the sensor 17 at the time) are generated. The individual images 21 are each composed of numerous image points 20', each with different image, or gray, values. In the formation of the three-dimensional data set 19 from the individual images 21, the conversion or transformation (sorting in correct position) of the several image data 20, or gray values, into the new reference system, which may for example be a Cartesian coordinate system, is accomplished. At the same time, gaps are filled by interpolation. This transformation will be explained in more detail below with reference to FIG. 7. These steps of the process are performed using the calibration data.

If a dynamic data capture or acquisition is performed, an interpolation of time gaps takes place, in particular making use also of image data from different ECG cycles. In the absence of dynamic acquisition, this step is omitted.

Next comes the decision whether the respiratory status is to be taken into account or not. In the latter case, for example such data are eliminated and discarded where the respiratory activity transgresses a preassigned threshold.

The data obtained, finally, are so laid out that they may be used for a two-dimensional and/or a three-dimensional representation as well as for two-dimensional and/or three-dimensional quantification.

FIG. 7, in simplified schematic form, shows various two-dimensional images 21 generated in the volume to be examined, and their image planes BE1 to BE4. For the sake of simplicity of representation, it has been assumed that each of these image planes lies perpendicular to the plane of the drawing in FIG. 7. Also represented is a voxel 20 which is produced like all other voxels forming the transformed three-dimensional data set 19. In transformation of the raw data 18 into the data set 19, i.e. in the formation of the voxels 20 in the image processing system 1, first, for example, following a preassigned program routine, a voxel 20, or its position (coordinates) in the data set 19, is selected, and then an image or gray value is formed for this voxel according to a preassigned function or a preassigned algorithm, namely from the gray values of those image points 20' which lie closest in each instance to the voxel 20 in the image planes BE1 to BE4 and whose distance from the particular voxel 20 does not exceed a preassigned distance designated in FIG. 7 by C. The value C either is fixedly preassigned by the system itself, or may be set by the user of the system, at least within certain limits. Preferably, the formation of the image or gray value for the voxel 20 to be formed in each instance is accomplished by forming a "weighted sum" or a weighted mean.

In so doing, as explained, in each instance those image points of each image plane BE1 to BE4 which. lie closest to the particular voxel 20 and whose distance from the voxel 20 does not exceed the maximum distance C are taken into account. These image points are designated in FIG. 7 as BP1 (on image plane BE1), BP2 (on image plane BE2), BP3 (on image plane BE3) and BP4 (on image plane BE4). The distances between the voxel 20 and the particular image point BP1 to BP4 are designated respectively X1, X2, X3 and X4. Taking account of this maximum allowable distance C and the distances X1 to X4, the following weights result for determining the image and gray values for the image points BP1 to BP4:

W1=C-X1
W2=C-X2
W3=C-X3
W4=C-X4

The image or gray values of image points BP1 to BP4 are respectively G1 for image point BP1, G2 for image point BP2, and so forth.

For the gray value GV of the current voxel, we then have:

$$GV=(G1*W1+G2*W2+G3*W3+G4*W4)/(W1+W2+W3+W4)$$

"G1*W1 means C1 multiplied by W1, G2*W2 means G2 multiplied by W2 and so on."

It will be understood that the current image or gray value GV may alternatively be determined according to some other mathematical function or some other algorithm, for example, such that when an image point BP for a given voxel 20 exists in an image plane BE and the distance is less than a preassigned minimum, then the gray value of that image point itself continues to be used as gray value GV, without going through the formation of a weighted mean in the manner just described.

It will be understood further that the formation of the value GV takes place for all voxels 20, to wit in such manner as to generate a complete, three-dimensional data set 19.

I claim:

1. A method of generating a diagnostically usable three-dimensional image data set (19) of a volume of a body under examination, said method comprising the steps of:

using an ultrasonic apparatus (6) with an ultrasonic head (7);

freely guiding said ultrasonic head (7) along said body under examination whereby a sequence of ultrasonic single images are generated in different image planes (BE1, BE2, BE3, BE4) of said volume to be examined;

transmitting said sequence of ultrasonic single images to an image processing system (1) connected to the ultrasonic apparatus;

determining the position and orientation of said ultrasonic head (7) and therefore the spatial location of the image plane of each ultrasonic single image, said determination being performed by a position sensor system (8) during generation of said sequence of ultrasonic single images, said position and orientation being determined in relation to the three degrees of freedom in translation and rotation, said sensor system (8) being an electromagnetic system whose receiver (10) is provided on said ultrasonic head (7);

transmitting said position and orientation data of said sensor system to said image processing system (1);

storing said ultrasonic single images as raw data together with an image header containing at least said position and orientation data, said raw data forming data set (18) consisting of a plurality of voxels (20);

forming a corresponding image or gray value for each voxel (20) according to a preassigned algorithm by measuring the image or gray values of those image points (20') which are closest in each instance to the current voxel (20) in the single images or their image planes (B1 to B4) and whose distance from the current voxel (20) does not exceed a preassigned maximum allowable distance (C) and using the measurements in said preassigned algorithm to determine said image or gray value for each voxel; and transforming the locations of said voxels (20) to a common coordinate system and transforming said raw data set (18) into said three-dimensional data set (19), whereby the volume of the body under examination is tomographically captured.

2. Method according to claim 1 wherein the receiver (10) of said sensor system is provided on the ultrasound head (7) or on the holder (17) attached to the ultrasound head, and in that the image processing system (1) calibrates the position and orientation data supplied by the sensor system with the use of parameters that take into account the spatial relationship between the receiver (10) of the sensor system and its orientation in space and the location of the image plane of the ultrasound head (7).

3. Method according to claim 2 wherein the image processing system (1) calibrates the position and orientation data in a subsequent processing phase following the storing of said ultrasonic single images as raw data.

4. Method according to claim 2 wherein the image processing system (1) calibrates the position and orientation data during the storing of said ultrasonic single images as raw data, and in that the calibrated position and orientation data are stored in the respective image header.

5. Method according to claim 1 further comprising the steps of connecting an electrocardiograph to the image-processing system (1) generating a signal defining an ECG cycle such as a signal representing the R wave of the ECG cycle with said electrocardiograph, storing in the image header a value which represents the phase position between such a defined point in time of the ECG cycle and the input of an ultrasound single image in the image-processing system.

6. Method according to claim 5 wherein, for generating a three-dimensional static data record, the transmission of ultrasound images into the image-processing system (1) takes place synchronously with the ECG cycle, in each instance in a predetermined time window of the ECG cycle.

7. Method according to claim 5 further comprising the steps of generating a three-dimensional dynamic data record (19, 19'), transmitting ultrasound single images into the image-processing system (1) continuously, and storing the image values in the three-dimensional data record (19, 19') in accordance with the phase position in the ECG cycle in the image-processing system.

8. Method according to claim 1, characterized in that a device (13) for capturing the respiratory cycle is used, and in that a measured value, which determines the phase position in the respiratory cycle, is stored in the image header.

9. Method according to claim 1 characterized in that in the transformation, first the current voxel (20) or its position (coordinates) is selected according to a preassigned program routine, and then the image or gray value of the voxel (20) is formed.

10. Method according to claim 1, further comprising the step of fixedly preassigning the value (C) of the maximum allowable distance.

11. Method according to claim 1, further comprising the step of adjusting the value (C) of the maximum allowable distance.

12. Method according to claim 1 wherein the image or gray value for the current voxel (20) is formed by forming a weighted sum or a weighted average according to the formula $$GV=(G1*[C-X1]+G2*[C-X2]+ \ldots +Gn*[C-Xn])/([C-X1]+[C-X2]+ \ldots +[C-Xn])$$

where

GV is the image or gray value of the current voxel (20), G1 . . . Gn are the image or gray values of the image points in neighboring single images, closest to the current voxel (20), X1, X2, . . . Xn are the respective distances of these image points of the single images from the current voxel (20), and C is the maximum allowable distance.

13. A device for generating a diagnostically usable three-dimensional image data set (19) of a volume of a body under examination, said device comprising:

an ultrasonic apparatus (6) with a freely guided ultrasonic head (7) which generates a sequence of ultrasonic single images in different image planes of (BE1, BE2, BE3, BE4) of the volume to be examined;

an image processing system (1) connected to the ultrasonic apparatus (6) to which system the sequence of ultrasonic single images is supplied;

a position sensor system (8) that determines the position and orientation of said ultrasonic head (7) and therefore the spatial location of the image plane of each ultrasonic single image, the location being determined in relation to the three degrees of freedom in translation and rotation, said sensor system (8) being an electromagnetic system whose receiver (10) is provided on said ultrasonic head (7);

means for transmitting said position and orientation data of said sensor system to said image processing system (1) in which said ultrasonic single images are first stored as raw data in this phase of data acquisition together with an image header containing at least said position and orientation data, said raw data forming data set (18) consisting of a plurality of voxels (20);

means for forming a corresponding image or gray value for each voxel (20) according to a preassigned algorithm by measuring the image or gray values of those image points (20') which are closest in each instance to the current voxel (20) in the single images or their image planes (B1 to B4) and whose distance from the current voxel (20) does not exceed a preassigned maximum allowable distance (C) and using the measurements in said preassigned algorithm to determine said image or gray value for each voxel; and means for transforming the locations of said voxels (20) to a common coordinate system and transforming said raw data set (18) into said three-dimensional data set (19), whereby the volume of the body under examination is tomographically captured.

14. Device according to claim 13 wherein the receiver (10) of said sensor system is provided on the ultrasound head (7) or on the holder (17) attached to said ultrasound head, and in that the image processing system (1) has means for calibrating the position and orientation data supplied by the sensor system with the use of parameters that take into account the spatial relationship between the receiver (10) of the sensor system and its orientation in space and the position of the image plane of the ultrasound head (7).

15. Device according to claim 13, characterized in that the calibration of the position and orientation data is effected in a subsequent processing phase following the data-acquisition phase.

16. Device according to claim 14 wherein the image processing system (1) calibrates the position and orientation data during the storing of said ultrasonic single images as raw data, and in that the calibrated position and orientation data are stored in the respective image header.

17. Device according to claim 13 wherein an electrocardiograph is connected to the image-processing system (1) and generates a signal defining an ECG cycle such as a signal representing the R waves of the ECG cycle, where the image-processing system (1) has means for storing a value which represents the phase position between such a defined point in time of the ECG cycle and the input of an ultrasound single image in the image-processing system.

18. Device according to claim 17 wherein the means for transmitting transmits the ultrasound images into the image-processing system (1) synchronously with the ECG cycle, in a predetermined time window of the ECG cycle.

19. Device according to claim 17 wherein the means for transmitting transmits the ultrasound single images into the image-processing system (1) continuously, and the image-processing system has means for storing the image values in the three-dimensional data record (19, 19') in accordance with the phase position in the ECG cycle.

20. Device according to claim 13 further comprising a means (13) for capturing the respiratory cycle connected to said image processing system (1).

21. Device according to claim 13, further comprising a preassigned program routine for first selecting the current voxel (20) or its position and then forming the image or gray value of the voxel (20) during the transformation.

22. Device according to claim 13 further comprising means for fixing the value (C) of the maximum allowable distance.

23. Device according to claim 13 further comprising means for adjusting the value (C) of the maximum allowable distance.

24. Device according to claim 13 further comprising means for forming the image or gray value for the current voxel (20) by formation of a weighted sum or a weighted average according to the formula $$GV = (G1*[C-X1] + G2*[C-X2] + \ldots + Gn*[C-Xn]) / ([C-X1] + [C-X2] + \ldots + [C-Xn])$$

where

GV is the image or gray value of the current voxel (20),

G1 . . . Gn are the image or gray values of the image points in neighboring single images, closest to the current voxel (20), X1, X2, . . . Xn are the respective distances of these image points of the single images from the current voxel (20), and C is the maximum allowable distance.

* * * * *

UNITED STATES PATENT AND TRADEMARK OFFICE
Certificate

Patent No. 5,924,989                                                            Patented: July 20, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Hans Polz, Wartenberg, Germany; Hartmut Konig, Moosberg, Germany; and Markus Marquart, Eching, Germany.

Signed and Sealed this Thirtieth Day of April 2002.

*MARVIN M. LATEEF*
*Supervisory Patent Examiner*
*Art Unit 3737*